United States Patent [19]
Narayanan

[11] Patent Number: 5,776,856
[45] Date of Patent: Jul. 7, 1998

[54] SOLUBLE POLYMER BASED MATRIX FOR CHEMICALLY ACTIVE WATER INSOLUBLE COMPONENTS

[75] Inventor: Kolazi S. Narayanan, Wayne, N.J.

[73] Assignee: ISP Investments Inc., Wilmington, Del.

[21] Appl. No.: 795,022

[22] Filed: Feb. 4, 1997

[51] Int. Cl.$^6$ .................. A01N 25/30; C05G 5/00; C08L 33/00

[52] U.S. Cl. .................. 504/116; 424/407; 514/950; 71/904; 71/DIG. 1

[58] Field of Search .................. 504/116; 424/407; 514/950; 71/904, DIG. 1

[56] References Cited

U.S. PATENT DOCUMENTS

| | | | |
|---|---|---|---|
| 5,580,578 | 12/1996 | Oshlack et al. | 424/468 |
| 5,597,574 | 1/1997 | Narayanan et al. | 424/401 |
| 5,629,261 | 5/1997 | Narayanan et al. | 504/116 |

*Primary Examiner*—S. Mark Clardy
*Attorney, Agent, or Firm*—Marilyn J. Maue; William J. Davis; Walter Katz

[57] ABSTRACT

This invention relates to a water soluble matrix composition comprising an anionic surfactant, a $C_6$ to $C_{18}$ alkyl pyrrolidone, urea and a water insoluble copolymer of vinyl pyrrolidone with not more than 50 wt. % of a comonomer selected from the group of an α-olefin, vinyl acetate, an acrylic or methacrylic acid ester and methacrylamide as a free flowing particulate solid which matrix is suitably mixed with a water insoluble, chemically active component, such as an agrochemical, to provide a clear sprayable film forming emulsion, such as a non-leachable film on a plant or other substrate surface. The invention also relates to the method of preparing the matrix and to the incorporation of an agrochemical concentrate and plant spray composition.

18 Claims, No Drawings

SOLUBLE POLYMER BASED MATRIX FOR CHEMICALLY ACTIVE WATER INSOLUBLE COMPONENTS

BACKGROUND OF THE INVENTION

Water soluble matrices for water insoluble agrochemically active chemicals in effective concentration are highly desirable and, for environmental considerations, are much preferred over dusts in the treatment of crops or other vegetation. Heretofore such aqueous systems have not met with great success because they are readily removed by rainwater. Proposals to incorporate film forming components in the formulation have been equally disappointing since non-toxic polymers which possess such properties are themselves water insoluble and are only able to form coarse suspensions which are highly unstable. Usually the inert water soluble or water insoluble matrix composition, which is a mixture of organic solvents and surfactants, is packaged and shipped to the location of use where it is mixed with the active agrochemical concentrate and diluted for immediate use by carefully monitoring the dosage to an effective, plant tolerant level. Obviously, a matrix in the form of directly soluble free flowing particles incorporating the insoluble agrochemical for use as a stable, non-leachable, film forming spray would offer considerable advantages. Further, such a stable composition which incorporates the active chemical in a substantially high concentration such that final dilution with water automatically produces the recommended plant treatment dosage in a clear microemulsion, is even more desirable.

Accordingly, it is an object of this invention to achieve the above stated goals by providing a soluble matrix composition which is capable of incorporating an insoluble active component and which is commercially conducive to producing a stable film forming aqueous spray.

Another object of this invention is to provide a water soluble matrix for an insoluble agrocultural chemical which promotes its uniform dispersion in a clear, film forming, aqueous microemulsion.

Another object of this invention is to provide a method for the preparation of the present matrix and a method for the incorporation and use of an insoluble active component such as an agrochemical.

These and other objects of this invention will become apparent from the following description and disclosure.

THE INVENTION

In accordance with this invention there is provided a water soluble, free flowing particulate matrix composition which comprises (a) between about 20 and about 40 wt. % of a $C_6$ to $C_{18}$ alkyl lactam; (b) between about 25 and about 75 wt. % urea; (c) between about 3 and about 20 wt. % surfactant as an anionic surfactant or an anionic/non-ionic surfactant mixture; and (d) between about 5 and about 15 wt. % of a water insoluble copolymer of a N-vinyl lactam containing not more than 50 wt. % of a comonomer selected from the group of vinyl acetate, an α-olefin, an acrylic or methacrylic acid ester, methacrylamide and mixtures thereof. In the above composition, the urea component is complexed with the copolymer to provide a water soluble solid in the presence of anionic surfactant which, upon dilution with water, provides a clear, single phase solution. The matrix is mixed with a water insoluble, chemically active component, such as an agrochemical concentrate in a liquid or a solid state, so as to produce upon recommended dosage dilution in water a clear sprayable emulsion in which the active component is uniformly dispersed.

Typically the agrochemical concentrate in the liquid state contains the active component in a concentration of between about 1 and about 80 wt. % along with an emulsifier, an organic solvent such as an alkyl ester, an alkyl naphthalene, a ketone, etc. and optionally a defoaming and/or a dispersing agent. When employed in solid form, the concentrate, in addition to the active component in the above concentration, contains an inert particulate solid such as talc, clay, alumina, silica, gum, etc. and may also contain a thickener.

In accordance with the present invention, between about 1 and about 90 wt. % of the matrix is combined with between about 99 and about 10 wt. % of the active concentrate and the concentration of the active agrochemical in the resulting mixture can be as high as 30 wt. %. Before use, the matrix/condensate mixture is diluted with water to the recommended active dosage level, usually from a few ppm to about 3 wt. %, depending on the efficacy or toxicity of the active chemical or a selected active chemical mixture the substrate or plant undergoing treatment. Alternatively, the concentrate can be diluted with water to form a dispersion before combining with the solid matrix material.

Both the matrix itself and the matrix/active composition products of this invention attain many benefits heretofore unachievable which include increased spreadability on a substrate surface, e.g. a plant surface, gradual penetration of the agrochemical into plant tissue as well as achieving rainfastness and stability of the spray formulation. The matrix alone provides a readily soluble, free flowing powder or granules which may or may not contain the active component and which can be stored for extended periods without deterioration and which can be shipped in water soluble or water dispersible bags. The concentrate agrochemical/matrix product mixture contains the agrochemical in an adequately high concentration so that upon dilution with water the proper non-phytotoxic spray emulsion or microemulsion is automatically obtained thus eliminating guesswork in monitoring the addition immediately prior to use. Finally, the present active/matrix composition achieves superior uniformity as the copolymer/urea complex aids in the intimate dispersion of the insoluble active material.

The alkyl lactam component of the present composition is preferably N-octyl- and/or N-dodecyl-pyrrolidone and or the correspondingly substituted caprolactam. The preferred copolymer is one containing less than 30 wt. % of the olefinically unsaturated comonomer in a graft polymer structure.

A preferred method of preparing the matrix composition involves forming a solution of components (a) through (d) in an organic solvent common to both the copolymer and urea, e.g. tetrahydrofuran, glycol ether etc. or in water to form a dispersion and subjecting the resultant mixture to spray drying, freeze drying or evaporation to dryness. The copolymer/urea complex which converts the insoluble copolymer to soluble form, is thus formed at between about room temperature and about 75° C. The complexing of urea with the copolymer in place of the long chain lactam provides increased spreadability resulting in the formation of a rainfast film on the substrate surface. Such a film is particularly useful in agrochemical sprays and in paint or caulking compositions in concentrated form.

Examples of suitable defoaming agents which are optionally introduced into the present matrix/active formulations include the sodium salts of long chain fatty acids. Dispersants which are optionally added to the active concentrate include lignin sulfonate, naphthalene sulfonate etc.

Suitable anionic surfactants employed in the present formulation include sulfates, sulfonates and phosphate esters and salts thereof. For example, the alkali metal salts of a $C_8$ to $C_{22}$ aliphatic compound such as sodium dodecyl sulfate or sulfonate or an alkyl aromatic sulfate or sulfonate, as well as ethoxylated derivatives thereof or ethoxylated alkyl phenyl phosphate esters. Of these, sodium dodecyl sulfate and Na or Ca dodecyl benzene sulfonate are preferred.

The agriculturally active component of the present invention is normally a water-immiscible or oily liquid or solid. These include insecticides, plant growth regulants, nemocides, plant nutrients, herbicides, fungicides, fumigants and pesticides in general.

As used herein, the term "agriculturally active chemical" includes compounds and mixtures thereof which can be used as agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, and the like, as well as any other chemicals having properties which are suitable for agricultural uses in terms of application to plants or animals or domestic uses for controlling insects and pests. Particularly, such chemicals would normally take the form of water-immiscible or oily liquids and/or solids which is substantially insoluble in water. By the term "substantially insoluble", it is meant that for all practical purposes, the solubility of the compound in water is insufficient to make the compound practicably usable in an agricultural end use without some modifications either to increase its solubility or dispersability in water, so as to increase the compound's bioavailability or avoid the use of excessively large volumes of solvent.

Agricultural chemicals normally take the form of water-immiscible or oily liquids and/or solids. Suitable agriculturally active chemicals which can be used with the present invention include insecticides, herbicides and fungicides. Typical insecticides include cyclocompounds, carbamates, animal and plant derivatives, synthetic pyrethroids, diphenyl compounds, non-phosphates, organic phosphates, thiophosphates, and dithiophosphates. (See *Agricultural Chemicals*, Book I, *Insecticides*, 1989 Revision by W. T. Thomson, Thomson Publications.) Typical of the insecticides are:

cyclocompounds:
6,7,8,9,10,10-hexachloro-1,5,5a,6,9,9a-hexahydro-6,9-methano-2,4,3-benzodioxathiepin-3-oxide benzodiooxathiepin-3-oxide
carbamates:
2-isopropyl phenyl-N-methyl carbamate;
2-(1,3-dioxolan-2yl) phenylmethyl carbamate;
2,3-isopropylidine dioxyphenyl methyl carbamate;
animal and plant derivatives:
chlorinated hydrocarbons derived from Southern pine;
naturally occurring lactone glycoside;
synthetic pyrethroids:
(±) alpha-cyano-3-phenoxybenzyl (±) cis, trans 3-(2,2-dichlorovinyl)-2,2-dimethyl cyclopropane carboxylate;
(±) cyano (3-phenoxyphenyl methyl
(±)-4-(difluoromethyoxy) alpha-(1-methylethyl) benzene acetate;
D-allethrin
permethrin
tetramethrin
cypermethrin
piperonyl butoxide (synergist)
phenoxy compounds and non-phosphates:
2,2-bis(p-methoxy phenyl)-1,1,1-trichloroethane;
1,3,5,tri-n-propyl-1,3,5-triazine-2,4,6 (1H,3H,5H) trione;
ethyl (2E, 4E)-3,7,11-trimethyl-2,4-dodeca dienoate:
1-decycloxy 4-[(7-oxa-oct-4-ynyl)]-oxybenzene;
organic phosphates:
dimethyl phosphate ester of 3-hydroxy-N,N-dimethyl-cis-crotonamide;
2-chloro-1-(2,4-dichlorophenyl) vinyl diethylphosphate;
4-(methyl thio) phenyl dipropyl phosphate;
thiophosphates:
O,O-diethyl-0-4-nitrophenyl phosphorothioate;
O,O-diethyl-0-(2-isopropyl-6-methyl-5-pyrimidinyl) phosphorothioate;
2-diethylamino-G-methyl pyrimidine-4-yl dimethyl phosphorothioate;
dithiophosphates:
O,O-dimethyl phosphorodithioate ester of diethylmercapto succinate;
0-ethyl-S-phenyl ethyl phosphorodithioate.

Typical herbicides include phenoxy compounds, benzoic, acetic, and phthalic acids, aniline derivatives, nitriles, amides, acetamides, anilides, carbamates, thiocarbamates, heterocyclic nitrogen derivatives, triazines, pyridines, pyridazones, picolinic acid, urea derivatives, phosphates etc. (see *Agricultural Chemicals*, Book II, Herbicides, 1986-87 Edition, W. T. Thomson, Tomson Publications, Fresno, Calif. 93791). Exemplary of these compounds are:

phenoxy compounds:
2,4-dichlorophenoxy acetic acid;
2,4,5-trichlorophenoxy acetic acid;
4-(2,4-dichlorophenoxy)butyric acid;
S-ethyl-2-methyl-4-chlorophenoxy thioacetate;
2-methyl-4-chlorophenoxy acetic acid;
methyl 5-(2,4-dichlorophenoxy)-2-nitrobenzoate;
benzoic and acetic acids of phthalic compounds:
3,6-dichloro-o-anisic acid;
4-chloro-2-oxo-benzothiazolin-3-yl acetic acid;
N-1-naphthyl phthalamic acid;
nitriles and aniline derivatives:
3,5-dibromo-4-hydroxybenzonitrile;
α,α,α-trifluoro-2,6-dinitro-N,N-dipropyl-p-tolinidine;
N-(1-ethylpropyl)-2,6-dinitro-3,4-xylidine;
anides, acetamides and anilides:
N,N-diethyl-2-(1-naphthalenyloxy)propionamide;
2,6-dimethyl-N,2'-methoxy ethyl chloro-acetanilide;
3',4'-dichloropropionanilide;
a-chloroacetic-N-(3,5,5-trimethylcyclohexen-1-yl)-N-isopropylamide;
4-benzyl-N-isopropyl trimethyl acetamide;
thiocarbamates:
S-ethyl dipropyl thiocarbamate;
urea derivatives:
3- (5-tert-butyl-3-isoxazoyl) -1,1-dimethyl urea;
N-(2,4,6-trifluorobenzoyl)-N'-[2,5-dichloro-4-(1,1,2,3,3,3-hexafluoropropyloxy) phenyl]urea;
pyrrolidone derivatives:
1-(m-trifluoromethylphenyl) -3-chloro-4-chloromethyl-2 -pyrrolidone;
amino acid derivatives:
methyl N-benzoyl-N-(3-chloro-4-fluorophenyl)-DL alarinate;
N-chloroacetyl-N-(2,6-diethylphenyl)glycine ethyl ester;
carbamates:
isopropyl-m-chlorocarbanilate;
3-ethoxy(carbonyl aminophenyl)-N-phenylcarbamate;
heterocyclics:

4-amino-3,5-dichloro-6-fluoro-2-pyridyloxy acetic acid;
4- (1, 2-dimethyl-N-propylamino) -2-ethylamino-6-methyl thio-S-triazine;
2-[4,5-dihydro-4-methyl-4-(1(-methylethyl)-5-oxo 1,H-imidazoyl-2-yl-3-byridine] carboxylic acid;
2-(3,5-dichlorophenyl)-2-(2,2,2-trichloroethyl) oxinane;
butyl-9-hydrofluorene-(9)-carboxylate;
2-[1-(ethoxyimino)butyl]-3-hydroxy-5-(2H-tetrahydrothiopyran-3-yl) 2-cyclohexene-ione;
2-(2-chlorophenyl)methyl-4,4-dimethyl-3-iso oxazolidinone;

phosphates:

O-ethyl-0-(3-methyl-6-nitrophenyl) N-sec-butyl phosphoro thioamidate.

Typical fungicides are those disclosed in *Agricultural Chemicals*, Book IV, Fungicides, 1989 Revision). These include:

organic compounds:
2, 5-dimethyl-N-cyclohexyl-N-methoxy-3 -furan carboxamide;
5-ethyloxy-3-trichloromethyl-1, 2, 4-thiadiazole;
3-(2-methylpiperidino)propyl-3,4-dichloro-benzoate;
N,N-[1,4-piperazinediyl bis (2,2,2-trichloro) ethylidene] bis (formamide);
tetramethyl thiuram disulfide;
O-ethyl-S,S-diphenyl dithiophosphate;
5,10-dihydro-5,10-dioxo naphtho(2,3,9)-p-2,3-dicarbonitrile;
2-(thiocyanomethyl thio)benzothiazole;
α2-[(4-chlorophenyl) ethyl] -α-(1, 1-dimethyl ethyl)-1,H-1, 2,4-triazole-1-ethanol;

morpholines:

N-tridecyl-2,6-dimethyl morpholine;
4,N-dodecyl-2,6-dimethyl morpholine;

Typical fumigants, growth regulators, repellants, and rodenticides are those disclosed in *Agricultural Chemicals*, Book III, Fumigants, 1988-1989 Revision. Examples of these include:

growth regulants:
1,2-dihydro-6-ethoxy-2,2,4-trimethylquinoline;
2-chloroethyl phosphoric acid;
4-[(acetamino)methyl]-2-chloro-N(2,6-diethyl phenyl) acetamide;
benzoic acid 3,6-dichloro-2-methoxy-2-ethoxy-1-methyl-2-oxoethyl ester;

repellants:

O,O-dimethyl-O-[(4-methyl thio)-m-tolyl] phosphorothioate;
tert-butyl sulfenyl dimethyl dithiocarbamate;

seed softeners:
2-chloro-6-(trichloromethyl)pyridine;
5-ethoxy-3-trichloromethyl-1,2,4-thiadiazole;
N-phenyl-N',1,2,3-thiadiazol-5-yl urea;

Pesticides may be characterized by their physical properties, depending on their physical state at normal or ambient conditions, i.e., between 40° and 90° F. and their solubility or miscibility with water or other common organic solvents, eg., aromatics, such as toluene, xylene, methylated and propylated naphthalenes and aliphatic solvents.

Based on physical properties, pesticides may be classified into two groups. The first group includes those which are oily liquids at ambient temperatures and are miscible with water. These include:

common esters of the following:
2,4-dichlorophenoxy acetic acid,
2,4,5-trichlorophenoxy acetic acid,
2-(2,4-dichlorophenoxy)propionic acid,
2-(2,4,5-trichlorophenoxy)propionic acid,
2,4-dichloro butyric acid,
2-methoxy-3,6-dichloro benzoic acid,
2-methyl-4-chlorophenoxy acetic acid, Examples of other pesticides include:
piperonyl butoxide 3,4-methylenedioxy-6-propyl benzyl butyl diethylene glycol ether,
O,O-diethyl-O,2,5-dichloro-4-bromophenyl thionophosphate (Bromophos ethyl),
N-(2-mercaptoethyl)benzene sulfenamide (BETASAN®),
isobornyl thiocyanoacetate (THANITE®),
ioxynil ester of octanoic acid,
molinate S-ethyl hexahydro-1H-azepine-1-carbothioate,
O,O-dimethyl-(2-diethylamine-4-methyl-6-pyrimidinyl) carbamate (PP 511),
O,O-diethyl-O-(2-diethylamine-4-methyl-6-pyrimidinyl) phosphorocarbamate (PP211),
octachloro-4,7-methano-3a,4,7,7a-tetra-hydroindane (Chlordane),
5-ethoxy-3-(trichloromethyl)-1,2,4-thiadiazole (TERRAZALE®),
ethyl-S,S-dipropylphosphodithioate (MOCAP®),
S-ethyl dipropylthiocarbamate (EPTAM®),
S-ethyl diisobutylthiocarbamate (SUTAM®),
S-propyl-dipropylthiocarbamate (VERNAM®),
S-propyl butylethylthiocarbamate (TILLAM®),
S-ethyl ethylcyclohexylthiocarbamate (RO-NEET®)
S-(1,2-dicarboxyethyl)-O,O-dimethyl phosphoro dithioate (Malathion),
O,O-diethyl-O-(2-isopropyl-4-methyl-6-pyrimidinyl) phosphorothioate (Diazinon),
O-ethyl-S-phenylethylphosphonodithioate (DYFONATE®),
octachlorocamphene (Toxaphene),
3,5-dibromo-4-hydroxy benzonitrile ester of octanoic acid (Bromoxynil),
2-chloro-N,2,6-diethylphenyl-N-methoxymethy acetamide (Lasso®),
2,3-dichloroallyl-N,N-diisopropylthiolcarbamate (Diallate S),
2,33-trichloroallyl-N,N-diisopropyl-thiolcarbamate (Triallate S). p The second group comprises those pesticides which are solids at ambient temperatures and, for all practical purposes, insoluble in water. Examples of these include:
2,4,5-trichlorophenoxy acetic acid (2,4,5-T),
3-(p-chlorophenyl)-1,1-dimethyl urea (Monuron),
3-(3,4-dichlorophenyl)-1,1-dimethyl urea (Diuron),
5-bromo-3-sec-butyl-6-methyl uracil (Bromacil),
5-bromo-3-isopropyl-6-methyl uracil (Isocil),
3-(3,4-dichlorophenyl)-1-methoxy-l-methyl urea (Linuron)
2-chloro-4-ethylamino-6-isopropylamino-S-triazine (Atrazine),
2-chloro-4,6-bis(ethylamino)-S-triazine (Simazine),
dodecylguanidine acetate (Dodine),
tetramethylthiuram disulfide (Thiram),
N-(mercaptomethyl)phthalimide S-(O,O-dimethylphosphorodithioate) (IMIDAN®),
γ-1,2,3,4,5, 6-hexachlorocyclohexane (Lindane),
N-trichloromethylphthalimide (Folpet),
S-(4,6-diamino-1,3,5-triazin-2-yl methyl) dimethylphosphorothiol thionate (Manazon),
4-chloro-2-butynyl-m-chlorocarbanilate (Barban),
2-methoxy-3,5,6-trichlorobenzoic acid (Tricumba),
2,6-dinitro-N,N-dipropyl trifluoromethyl aniline (Trifluralin),
2,3-dihydro-5-carboxanilido-6-methyl-1,4-oxathiin (VITAVAX®), 2,4-dichlorophenoxy acetic acid,
4-(4-chloro-2-methylphenoxy)butyric acid,
2-(2,4-dichlorophenoxy)propionic acid,
3,5-diiodo-4-hydroxybenzonitrile (Ioxynil),
3,5-dibromo-4-hydroxybenzonitrile (Bromoxynil),
2,2-bis(p-methoxyphenyl)-1,1-trichloroethane (Methoxychlor),
4-(2-chlorophenylhydrazono)-3-methyl-5-isoxazolone (PP 781)*,
5-butyl-2-dimethylamino-4-hydroxy-6-methyl pyrimidine (PP 675)*,
5,6-dimethyl-2-dimethylamino-4-pyrimidinyl dimethylcarbamate (PP 062)*,
5-butyl-2-ethylamino-4-hydroxy-6-methyl pyrimidine (PP 149)*,
N'-(4-bromo-3-chlorophenyl)-N-methoxy-N-methylurea (C 6313),
2,4'dinitro-4-trifluoromethyl-diphenylether (C 6989),
N'-4-(chlorophenoxy) phenyl-NN-dimethylurea (Chloroxuron),
2,6-dichlorobenzonitrile (Dichlobenil),
N,N-dimethyl-2,2-diphenylacetamide (Diphenamid),
2,3,6-trichlorophenylacetic acid) (Fenac),
N'-(3-trifluoromethylphenyl)-NN-dimethylurea (Fluometuron),
4-ethylamino-2-methylthio-6-t-butyl-amino-1,3,5-triazine, (GS 14260),
Pentachlorophenol) (PCP),
3-cyclohexyl-6,7-dihydro-1H-cyclo-pentapyrimidine-2,4-(3H,5H)-dione, (Lenacil),
5-amino-4-chloro-2-phenyl-3-pyridazone (Pyrazon),
N'-(4-bromophenyl)-N-methoxy-N-methylurea (Metrobromuron),
N-(4-methoxybenzoyl)-N-(3,4-dichlorophenyl)-N',N'-dimethylurea (Metoxymarc),
N-butyl-N'-(3,4-dichlorophenyl)-N-methylurea (Neburon),
1,1-dimethyl-3-[3-(n-t-butyl carbamyloxy) phenyl] urea (NIA 11092),
2-(4-chloro-2 methylphenoxy)propionic acid (Mecoprop),
N'-(4-chlorophenyl)-N-methoxy-N-methylurea (Monolinuron),
2,4-dichlorophenyl-4-nitrophenylether (Nitrofen),
N-(3,4-dichlorophenyl)propionamide (Propanil),
2,3,5-trichloro-4-pyridinol (Pyriclor),
3'-chloro-2-methyl-p-volerotoluidide (Solan),
5-chloro-3-t-butyl-6-methyluracil (Terbacil),
3,4-dichlorobenzyl N-methylcarbamate (SIRMATE®),
2-Azido-4-ethylamino-6-t-butylamino-s-triazine (WL 9385),
2-chloro-N-isopropylacetanilide (Propachlor),
2-chloro-N-2,6-diethylphenyl-N-methoxymethyl acetamide (CP 50144),
2-chloro-N-(2 methyl-6-t-butylphenyl)acetamide (CP 31675),
3',4',-dichlorocyclopropane carboxanilide (Cypromid),
N,N-dimethyl-N'-phenylurea (Fenuron),
N'-(4-bromo-3-chlorophenyl)N-methoxy-N-methylurea (Chlorbromuron),
2-methylmercapto-4-ethylamino-6-isopropyl-amino-s-triazine (Ametryne),
2-methylmercapto-4,6-bis(isopropyl)amino-s-triazine (Prometryne),
dimethyl-2,3,5,6-tetrachloro-terephthalate (DCPA),
N-butyl-N-ethyl-2,2,2-trifluoro-2,6-dinitro-p-toluidine (Benefin),
2,6-dinitro-4-methylsulfonyl-N,N-dipropyl-aniline (Nitralin),
2,6-difluoro-3,5-dichloro-4-hydroxy pyridine (PP 493),
2,4,6-trichlorophenyl-4'-nitrophenyl ether (CNP),
pentachloro nitrobenzine,
methyl ester of 1-(butile carbamoyl)-2-benzimidazol carbamic acid (BENLATE®).

*Manufactured by Imperial Chemical Industries, Ltd.

The above agrochemicls are generally incorporated at the recommended dosage levels; although, because of the rainfast films and increased penetration into plant tissue, somewhat smaller dosages may be employed.

Having generally described the invention, reference is now had to the following examples which illustrate preferred embodiments of the invention but which are not to be construed as limiting to the scope thereof which is defined in the foregoing disclosure and in the appended claims.

EXAMPLE 1

PREPARATION OF AGROCHEMICAL CONCENTRATES AND TESTING OF THEIR AQUEOUS MICROEMULSIONS ON PLANTS

A flask containing 50 grams of urea and 15 grams of 50 wt. % vinyl pyrrolidone/50 wt. % $C_{16}$ α-olefin copolymer having a 45 g N-octyl pyrrolidone and 40 g of 29% aqueous solution of Na dodecyl sulfate was slurried with 200 g of $H_2O$. The resulting mixture was subjected to freeze drying at minus 90° C. under 500 militor for 24 hours whereupon a free flowing hydrophilic solid of the urea/copolymer complex was recovered. The solid may be ground to an average particle size of from 1 to 100 microns (μ), e.g. 50μin this example. This composition is composition A.

Inert Matrix 53.5 wt. % urea copolymer complex, 37.0 wt. % N-octyl pyrrolidone and 9.5 wt. % Na dodecyl sulfate.

To 100 grams of the freeze dried ground powder of composition A is added 2 grams of water insoluble insecticide CARBARYL (naphthyl methyl carbamate) and the resulting mixture was dry blended in a twin shell blender for 30 minutes. A free flowing powder of uniformly distributed active insecticide having the composition of about Total Composition (Dry Basis)

52.4 wt. % urea/copolymer complex, 36.2 wt. % N-octyl pyrrolidone, 9.8 wt. % anionic surfactant and 1.6 wt. % active insecticide is recovered.

After a period of 5 days, 50 g of the above stable composition is diluted with 1 liter of water to form a clear single phase microemulsion having suspended particles of 0.01–0.1 micron (μ) size.

The above microemulsion is introduced into a commercial tank equipped with a nozzle and sprayed over a field of mature cabbage heavily infested with cabbage worm. After 15 days, no infection is noted and examination showed that a rain resistant film had formed over the plant surface and the active component had effectively destroyed the cabbage worm and any larvae. Also no leaching of the composition into the soil around the plant takes place after drenching with water.

EXAMPLE 2

When the above procedure is repeated using fungicide chlorothalonil in place of CARBARYL on tomato plants infested with late blight and using the fungicide at dilution containing 40 ppm* active on tomato plants, the same rain resistant films spread on the plant surfaces and exerted gradual release of the active agrochemical into the plant tissues for eradication and recurrence of fungal infection thus advancing plant growth. In all instances, the recommended dosage of the agrochemical was employed. *50 g of total composition (dry basis) where chlorothanonil replaces CARBARYL is diluted in 2 liters of water to prove the spray solution.

The following illustrate other compositions of the present invention which may be employed in treating plants with substantially equal properties and effectiveness.

Formulation 1

60 wt. % spray dried water insoluble vinylpyrrolidone/α-$C_{16}$ olefin (50/50) copolymer complexed with urea in ratio of 20 polymer/80 urea;

8 wt. % anionic surfactant (e.g. Na dodecyl benzene sulfonate);

2 wt. % active agricultural chemical, (metsulfuron-Methyl);

25 wt % N-octyl pyrrolidone; 5 wt. % dispersant (e.g. Na lignosulfonate).

Formulation 2

70 wt. % spray dried water insoluble vinylpyrrolidone-vinyl acetate (50:50) copolymer complexed with urea in a weight ratio of 40/60, 5 wt. % sodium lignosulfonate, 2 wt. % Morwet EFW (blend of naphthalenesulfonate formaldehyde condensate (WITCO), 20 wt. % N-octyl pyrrolidone, 3 wt. % crosslinked polyvinylpyrrolidone (disintegration agent).

COMPARATIVE EXAMPLE 3

Commercial herbicide formulation Banvil containing 4 lbs/gallon dimethyl amine salt of 3,6-dichloro-2-methoxy benzoic acid was diluted $^1/_{16}$with ground water and sprayed at the rate of 0.25 lbs active ingredient per acre on one acre of corn field infested with pigweed. The control of pigweed infestation was visually observed 8 weeks after treatment. It was found that only 59% of pigweed vegetation was eradicated.

EXAMPLE 3A

Example 3 was repeated with herbicide sprayed at half the rate (0.125 lbs/acre) as in Example 3, but using the matrix of composition A (Example 1), which was added to the spray solution at 0.4%, i.e. 4 Kg composition A in 1000 liters of aqueous spray solution. The pigweed growth was observed 8 weeks after treatment and found to be 90% eradicated.

EXAMPLE 4

Experiments similar to those described in Example 3 and Example 3A were repeated on a field planted with no-till corn in plots of 10 feet/24 feet. Plants were 20 inches tall. Control of weeds mostly (smooth pigweed) was assessed 10 weeks after treatment. The control was about 83% using composition of Example 3A, and 72% using composition of Example 3.

Further, the corn was harvested at the time of maturity, and plots treated with composition of Example 3A produced 20% higher yield compared to the plots treated with composition of Example 3.

EXAMPLES 5

Results on Rainfastness

A greenhouse trial with a laboratory rainfall simulator developed on the principle of droplet formation from needle tips showed increased rainfastness of Dicamba* based on shoot fresh weights of velvetleaf 28 days after treatment. Dicamba without composition A was not rainfast. Simulated rain at the rate of 12 mm rain/30 min was generated at 15 min, 30 min, 60 min, and 120 min after treatment. The lowest dose used for Dicamba, i.e. 92 g active/ha+0.2% solid composition A of Example 1 was added as tank mix in the spray solution and the simulated rain at 15 min. After treatment resulted in ½–⅔less fresh weed weight compared to treatment without composition A. Results were similar with delayed applications of rain (30 min, 60 min. after treatment) or with increased dose of the solid composition A.

* Dicamba is dimethyl amine salt of 3,6-dichloro-2-methoxy benzoic acid

EXAMPLE 6

400 g of non-selective systemic broad spectrum solid herbicide (ammonium salt of phosphonomethyl glycine) was blended with 200 g of the composition A of Example 1 in a "V" blender for a period of 20 minutes, and the resulting solid was transferred to a planetary mixer operating at setting 3. A paste was prepared using 40 g water and mixing for a period of 20 minutes. The wet paste was extruded using a bench-top extruder (1 mm screen). The extrudate was dried at 40° C. in a fluid-bed-drier for a period of 20 min. and then collected between 10 mesh and 40 mesh screen. About 500 g size-segregated extrudate was collected.

The above composition is diluted and applied on a grove of orange trees growing in plots of 10/24 feet. For comparative purposes, commercial liquid composition containing an equivalent of 3 pounds of the acid form of phosphonomethyl glycine/gallon formulated with a proprietary wetting agent as ROUNDUP®, was applied to an equal number of orange trees. The application rate of the spray solution was adjusted to a dose of 0.5 pound phosphonomethyl glycine acid form/acre. Simulated rain was applied at the rate of 1 cm for 30 min, one hour after completing the spraying operation. Plots treated with composition of Example 6, showed about 25% better control of species of weeds including barnyard grass, johnson grass, velvet leaf, morning glory and others than that of ROUNDUP.

EXAMPLE 7

Commercial fungicidal wettable powder formulations of mancozeb (zinc/manganese dithiocarbamate) containing ~80% active was mixed with composition A of Example 1 in the weight ratio of 80:20. A growing potato crop is treated with the above composition and compared with a potato plot treated with commercial mancozeb. Spraying the crop with the fungicidal compositions was carried out at dilutions producing about 1–2 lbs. active ingredient per acre. Plots treated with spray solutions containing composition A of Example 1 showed enhanced growth with practically no fungal infestation.

EXAMPLE 8

Following composition was mixed in a "V" blender, ground to <20μand air milled.

| | |
|---|---|
| (1) chlorothalonil | 60 g |
| (2) sodium lignosulfonate | 6 g |
| (3) Lomar D (high MW fraction naphthalene sulfonate formaldehyde condensate) | 4.5 g |
| (4) Morwet EFW (low MW fraction blend | 1.1 g |

| | |
|---|---|
| of naphthalene sulfonate formaldehyde condensate, WITCO) | |
| (5) Foam master (sodium salt of long chain fatty acid) (Defoamer) | 0.75 g |
| (6) Crosslinked polyvinyl pyrrolidone (disintegrant) | 3.0 g |
| (7) Compositon A of Example 1 | 40 g |
| (8) Calcium dodecylbenzene sulfonate (anionic) | 1 g |
| Total | 116.35 g |

100 g of the above powder was blended with a mixture of 4 g N-octyl pyrrolidone and 8 g of petroleum distillate (aromatic alkyl naphthelene fraction—Exxon 150] in a planetary mixer to produce a paste which was extruded and was dried as in Example 6.

The extrudate containing about 50% chlorothalonil is dispersed in water to a concentration containing about 50 ppm chlorothalonil and sprayed on growing peanut plants infested with fungi (powder mildew and late blight). The plants were free from infestation within 2 weeks after treatment. Crops sprayed with commercial chlorotholonil formulation did not control the fungus infestation.

When the above composition is repeated except that a plant growth promoter, e.g. Ethephon, is substituted for chlorothalonil, an increase in plant growth of at least 20% is achieved.

What is claimed is:

1. A water soluble, free flowing solid matrix composition which comprises:
    (a) between about 20 and about 40 wt. % of a $C_6$ to $C_{18}$ alkyl lactam,
    (b) between about 25 and about 75 wt. % urea,
    (c) between about 3 and about 20 wt. % of an anionic surfactant and
    (d) between about 5 and about 15 wt. % of a water insoluble copolymer of N-vinyl lactam monomer containing not more than 50 wt. % of a comonomer selected from the group consisting of an α-olefin, vinyl acetate, an acrylic acid ester, a methacrylic acid ester, methacrylamide and mixtures thereof; wherein said urea is complexed with said copolymer and said free-flowing solid has a particle diameter of from about 10 to about 350μ.

2. The matrix composition of claim 1 wherein the copolymer is the copolymer of N-vinyl lactam and an α-olefin.

3. The matrix composition of claim 2 wherein the concentration of said α-olefin is less than 30 wt. % and the N-vinyl lactam/α-olefin has a graft polymer structure.

4. The matrix composition of claim 1 wherein said alkyl lactam is selected from the group consisting of N-octyl pyrrolidone, N-dodecyl pyrrolidone, N-octyl caprolactam, N-dodecyl caprolactam and mixtures thereof.

5. The matrix composition of any one of claims 1 or 4 wherein the alkyl lactam is selected from the group consisting of N-octylpyrrolidone, N-dodecylpyrrolidone, N-octyl caprolactam and N-dodecyl caprolactam.

6. The matrix composition of any one of claims 1, 2, 3, or 4 wherein the anionic surfactant is selected from the group consisting of a sulfate, a sulfonate, a phosphate ester and mixtures thereof and alkali metal salts thereof.

7. A water soluble composition which comprises between about 1 and about 90 wt. % of the matrix of claim 1 and between about 99 and about 10 wt. % of a water insoluble active chemical as a film forming product.

8. The composition of claim 7 wherein the active chemical is a concentrate containing between about 1 and about 80 wt. % of an active water insoluble agrochemical and said composition is rain resistant.

9. The composition of claim 8 wherein the concentrate is in particulate form and contains an agrochemical carrier selected from the group consisting of talc, clay, alumina, silica and gum.

10. The composition of claim 8 wherein the concentrate is in liquid form and contains an organic solvent for the agrochemical and optionally a dispersing and/or a defoaming agent.

11. The water soluble composition of claim 7 wherein the alkyl lactam of said matrix is selected from the group consisting of N-octyl pyrrolidone, N-dodecyl pyrrolidone, N-octyl caprolactam, N-dodecyl caprolactam and mixtures thereof.

12. The water soluble composition of claim 7 wherein the copolymer of said matrix is a copolymer of an N-vinyl lactam and an α-olefin.

13. The water soluble composition of claim 12 wherein said α-olefin is α-hexadecene and the copolymer has a graft polymer structure.

14. The process of applying an effective biochemically active amount of the composition of claim 7 to a substrate.

15. The process of applying an effective fungicidal amount of the composition of claim 7 to a substrate.

16. The process of applying an effective herbicidal amount of the composition of claim 7 to a plant.

17. The process of preparing the matrix composition of claim 1 which comprises mixing components (a) through (d) under mild conditions of from about 20° C. to about 40° C. to form a water soluble urea/copolymer complex, drying the resultant complexed mixture to form a solid, reducing the solid to a particle size of from about 10 to about 350μ diameter to produce a free flowing, water soluble product and optionally adding to said product between about 10 and about 99 wt. % based on weight of matrix of a concentrate containing from about 1 to about 80 wt. % of a water insoluble chemically active compound.

18. The process of claim 17 wherein said concentrate is an agrochemical concentrate.

* * * * *